(12) United States Patent
Laughner et al.

(10) Patent No.: US 9,649,040 B2
(45) Date of Patent: May 16, 2017

(54) MEDICAL DEVICES FOR MAPPING CARDIAC TISSUE

(71) Applicant: Boston Scientific Scimed Inc., Maple Grove, MN (US)

(72) Inventors: Jacob I. Laughner, St. Paul, MN (US); Carlos Alberto Ricci, Apple Valley, MN (US); Vladimir V. Kovtun, Inver Grove Heights, MN (US); Shibaji Shome, Arden Hills, MN (US); Pramodsingh H. Thakur, Woodbury, MN (US); Allan C. Shuros, St. Paul, MN (US); Kevin J. Stalsberg, White Bear Lake, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 14/873,800

(22) Filed: Oct. 2, 2015

(65) Prior Publication Data
US 2016/0183809 A1 Jun. 30, 2016

Related U.S. Application Data

(60) Provisional application No. 62/059,587, filed on Oct. 3, 2014.

(51) Int. Cl.
*A61B 5/04* (2006.01)
*A61B 5/0245* (2006.01)
(Continued)

(52) U.S. Cl.
CPC ............ *A61B 5/0245* (2013.01); *A61B 5/046* (2013.01); *A61B 5/04014* (2013.01);
(Continued)

(58) Field of Classification Search
CPC . A61B 5/0245; A61B 5/04014; A61B 5/0422; A61B 5/0452
See application file for complete search history.

(56) References Cited

U.S. PATENT DOCUMENTS 5,772,604 A * 6/1998 Langberg ........... A61B 5/04525
600/518
5,795,304 A 8/1998 Sun et al.
(Continued)

FOREIGN PATENT DOCUMENTS

WO 9834540 A1 8/1998
WO WO0182099 A1 11/2001
(Continued)

OTHER PUBLICATIONS

Ahmad, A., et al. Evolution of Frequency of Composition for Atrial Arrhythmias. Jurnal Teknologi (Sciences & Engineering) 69(8):27-29, 2014.
(Continued)

*Primary Examiner* — Robert N Wieland
(74) *Attorney, Agent, or Firm* — Faegre Baker Daniels LLP

(57) ABSTRACT

Medical devices and methods for making and using medical devices are disclosed. An example system for mapping the electrical activity of the heart includes a catheter shaft. The catheter shaft includes a plurality of electrodes including a first electrode and a second electrode. The system also includes a processor. The processor is capable of collecting a first signal corresponding to the first electrode and a second signal corresponding to the second electrode. Collecting the first and second signals occurs over a time period. The processor is also capable of generating a first time-frequency distribution corresponding to the first signal, identifying a first dominant frequency value occurring at a first dominant frequency and a first time point, generating a second time-
(Continued)

frequency distribution corresponding to the second signal, identifying a second dominant frequency value occurring at a second dominant frequency and a second time point and determining an attraction point.

19 Claims, 11 Drawing Sheets

(51) Int. Cl.
   *A61B 5/042* (2006.01)
   *A61B 5/046* (2006.01)
   *A61B 5/00* (2006.01)

(52) U.S. Cl.
   CPC .......... *A61B 5/0422* (2013.01); *A61B 5/6852* (2013.01); *A61B 5/725* (2013.01); *A61B 5/726* (2013.01); *A61B 5/7253* (2013.01); *A61B 5/7257* (2013.01); *A61B 5/7203* (2013.01); *A61B 2505/05* (2013.01)

(56) References Cited

U.S. PATENT DOCUMENTS

| | | | |
|---|---|---|---|
| 6,070,094 | A | 5/2000 | Swanson et al. |
| 6,233,491 | B1 | 5/2001 | Kordis et al. |
| 6,735,465 | B2 | 5/2004 | Panescu |
| 7,376,458 | B2 * | 5/2008 | Palreddy ............ A61B 5/04525 600/509 |
| 7,751,873 | B2 | 7/2010 | de Voir |
| 8,010,186 | B1 | 8/2011 | Ryu |
| 8,543,195 | B1 | 9/2013 | Brockway et al. |
| 2004/0059237 | A1 | 3/2004 | Narayan et al. |
| 2004/0176696 | A1 | 9/2004 | Mortara |
| 2007/0299351 | A1 | 12/2007 | Harlev et al. |
| 2009/0143692 | A1 | 6/2009 | Brockway et al. |
| 2010/0014723 | A1 | 1/2010 | Addison et al. |
| 2010/0016693 | A1 | 1/2010 | Addison et al. |
| 2012/0184863 | A1 | 7/2012 | Harlev et al. |
| 2012/0232417 | A1 | 9/2012 | Zhang |
| 2013/0006131 | A1 | 1/2013 | Narayan et al. |
| 2013/0279881 | A1 | 10/2013 | Lu et al. |
| 2014/0051961 | A1 | 2/2014 | Badower et al. |
| 2014/0088395 | A1 | 3/2014 | Dubois et al. |
| 2014/0200467 | A1 | 7/2014 | Strom et al. |
| 2014/0330145 | A1 | 11/2014 | Brodnick |
| 2015/0342488 | A1 | 12/2015 | Laughner et al. |
| 2016/0007932 | A1 | 1/2016 | Laughner et al. |
| 2016/0183810 | A1 | 6/2016 | Laughner et al. |
| 2016/0183830 | A1 | 6/2016 | Laughner et al. |

FOREIGN PATENT DOCUMENTS

| | | |
|---|---|---|
| WO | 2005115232 A1 | 12/2005 |
| WO | WO2006037172 A1 | 4/2006 |
| WO | 2006060366 A2 | 6/2006 |
| WO | 2007137045 A2 | 11/2007 |
| WO | 2008035070 A2 | 3/2008 |
| WO | 2010054409 A1 | 5/2010 |
| WO | 2011093944 A1 | 8/2011 |
| WO | 2012044261 A1 | 4/2012 |
| WO | WO2012151301 A1 | 11/2012 |
| WO | 2015171742 A1 | 11/2015 |
| WO | 2015171898 A1 | 11/2015 |

OTHER PUBLICATIONS

Barquero-Perez, Oscar. Fundamental Frequency and Regularity of Cardiac Electrograms With Fourier Organization Analysis. IEEE Transactions on Biomedical Engineering, 57(9): 2168-2177, Sep. 2010.
Ciaccio, Edward J. et al: A new transform for the analysis of complex fractinated atrial electrograms:, BioMedical Engineering Online, Biomed Central Ltd, London, GB, vol. 10, No. 1, May 12, 2011, pp. 1-27.
Ciaccio, Edward J., et al., New Methods for Estimating Local Electrical Activation Rate During Atrial Fibrillation. Heart Rhythm 6:21-32, 2009.
Citi, et. al. A Real-Time Automated Point Process Method for Detection and Correction of Erroneous and Ectopic Heartbeats. IEEE Trans. Biomed. Eng., 59(10): 2828-2837, Oct. 2012.
International Search Report and Written Opinion issued in PCT/US2015/029441, mailed Jul. 23, 2015, 12 pages.
International Search Report and Written Opinion issued in PCT/US2015/029697, mailed Jul. 14, 2015, 13 pages.
International Search Report and Written Opinion issued in PCT/US2015/053747, mailed Jan. 5, 2016, 11 pages.
International Search Report and Written Opinion issued in PCT/US2015/053831, mailed Jan. 7, 2016, 15 pages.
International Search Report and Written Opinion issued in PCT/US2015/053842, mailed Dec. 17, 2015, 10 pages.
Minh Phuong Nguyen et al: "A new approach for frequency analysis of complex fractionated atrial electrograms", Proceedings of the 31st Annual International Conference of the IEEE Engineering in Medicine and Biology Society: Engineering the Future of Biomedicine, EMBC 2009, IEEE, Sep. 3, 2009, pp. 368-371.
Monzon, Sandra et al: "Sparse spectral analysis of atrial fibrillation electrograms", 2012 IEEE International Workshop on Machine Learning for Signal Processing, Sep. 23, 2012, pp. 1-6.
Riccio, Mark L., et al. Electrical Restitution and Spatiotemporal Organization During Ventricular Fibrillation. Circ Res., 84:955-963.
Swissa, Moshe, et al. Action Potential Duration Restitution and Ventricular Fibrillation Due to Rapid Focal Excitation. American Journal of Physiology—Heart and Circulatory Physiology, 282:H1915-H1923, 2002.
Tateno, et. al. Automatic Detection of Atrial Fibrillation Using the Coefficient of Variation and Density Histograms of RR and DeltaRR Intervals. Med. Biol. Eng. Comput., 39:664-671, 2001.
International Preliminary Report on Patentability issued in PCT/US2015/029441, mailed Nov. 15, 2016, 9 pages.

* cited by examiner

MEDICAL DEVICES FOR MAPPING CARDIAC TISSUE

CROSS-REFERENCE TO RELATED APPLICATION

This application claims priority to Provisional Application No. 62/059,587, filed Oct. 3, 2014, which is herein incorporated by reference in its entirety.

TECHNICAL FIELD

The present disclosure pertains to medical devices, and methods for manufacturing medical devices. More particularly, the present disclosure pertains to medical devices and methods for mapping and/or ablating cardiac tissue.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

SUMMARY

This disclosure provides design, material, manufacturing method, and use alternatives for medical devices. An example system for mapping the electrical activity of the heart includes a catheter shaft. The catheter shaft includes a plurality of electrodes. The plurality of electrodes includes a first electrode and a second electrode. The system also includes a processor. The processor is capable of collecting a first signal corresponding to the first electrode and a second signal corresponding to the second electrode. Further, collecting the first and second signals occurs over a time period. The processor is also capable of generating a first time-frequency distribution corresponding to the first signal, identifying a first dominant frequency value occurring at a first dominant frequency and a first time point, generating a second time-frequency distribution corresponding to the second signal, identifying a second dominant frequency value occurring at a second dominant frequency and a second time point and determining an attraction point. The attraction point is defined when the first dominant frequency value substantially relates to the second dominant frequency value.

Alternatively or additionally to any of the examples above, generating the first frequency distribution and the second frequency distribution utilizes at least one Fourier transform, Short-Time Fourier transform, or a Wavelet transform.

Alternatively or additionally to any of the examples above, generating the first time-frequency distribution and/or the second time-frequency distribution includes generating a spectrogram of the first signal and/or the second signal.

Alternatively or additionally to any of the examples above, the first or second dominant frequency value is substantially equal to a maximum frequency value, a chirp, a sustained maximum frequency value, a local maximum frequency and/or a dominant frequency characteristic.

Alternatively or additionally to any of the examples above, the system is capable of determining a dominant frequency threshold value and the maximum frequency and/or the local maximum frequency is greater than or substantially equal to the dominant frequency threshold value.

Alternatively or additionally to any of the examples above, the processor is configured to determine a dominant frequency threshold value, wherein the maximum frequency value and/or the local maximum frequency value is greater than or substantially equal to the dominant frequency threshold value.

Alternatively or additionally to any of the examples above, the first dominant frequency is substantially equal to the second dominant frequency and the first time point is substantially equal to the second time point.

Alternatively or additionally to any of the examples above, identifying a time interval and the time interval includes the first and second time points and the first dominant frequency value substantially relates to the second dominant frequency value over the time interval.

Alternatively or additionally to any of the examples above, the processor is configured to identify a time interval, wherein the time interval includes the first and second time points, and wherein the first dominant frequency value substantially relates to the second dominant frequency value over the time interval.

Alternatively or additionally to any of the examples above, the system is capable of collecting a signal from a third electrode over a time period and the processor generates a third dominant frequency value and the attraction point is defined when the first, second and third dominant frequency values substantially relate to each other.

Alternatively or additionally to any of the examples above, the system includes collecting a signal from a third electrode over a time period and the processor generates a third dominant frequency value and the processor is configured to define the attraction point when the first, second and third dominant frequency values substantially relate to each other.

Alternatively or additionally to any of the examples above, the system is capable of identifying a frequency interval and the frequency interval includes the first and the second dominant frequency values and the first dominant frequency value substantially relates to the second dominant frequency value over the frequency interval.

Alternatively or additionally to any of the examples above, the processor is configured to identify a frequency interval, wherein the frequency interval includes the first and the second dominant frequency values, and wherein the first dominant frequency value substantially relates to the second dominant frequency value over the frequency interval.

Alternatively or additionally to any of the examples above, the processor is capable of collecting a signal from a third electrode over a time period and the processor generates a third dominant frequency value and the frequency interval includes the first, the second and the third dominant frequency values, and the first, second and third dominant frequency values substantially relate to each other over the frequency interval.

Alternatively or additionally to any of the examples above, the processor is capable of generating a visual display, and the visual display includes displaying the at least one visual indicator, and the visual indicator corresponds to the first and/or second dominant frequency value.

Alternatively or additionally to any of the examples above, generating a visual display includes displaying at least one sinusoid corresponding to the first and/or second dominant frequency.

Alternatively or additionally to any of the examples above, the visual display includes displaying a phase map.

Alternatively or additionally to any of the examples above, the visual display includes a movie corresponding to the first or second dominant frequency and the first or second dominant frequency may change over multiple heart beats and over cardiac regions.

Alternatively or additionally to any of the examples above, the visual indicator is a color, texture or both.

Alternatively or additionally to any of the examples above, the visual display includes a movie displayed on an anatomical chamber.

Alternatively or additionally to any of the examples above, generating a visual display includes displaying at least one sinusoid corresponding to the first and/or second dominant frequency, displaying a phase map and/or the visual indicator is a color, texture or both.

Alternatively or additionally to any of the examples above, the first signal, the second signal, or both signals includes a plurality of modes corresponding to an anatomical region.

Alternatively or additionally to any of the examples above, the processor is capable of deconstructing the plurality of modes into different electrical patterns so that a tailored therapy can be directed to the anatomical feature.

Another example system for mapping the electrical activity of the heart includes a catheter shaft, a plurality of electrodes coupled to the catheter shaft and a processor coupled to the catheter shaft. The processor is capable of sensing a plurality of signals corresponding to the plurality of electrodes, generating a time-frequency distribution for each of the plurality of signals, utilizing a common dominant frequency characteristic to identify a common dominant frequency to one or more of the plurality of electrodes and creating a visual display corresponding to the common dominant frequency.

Alternatively or additionally to any of the examples above, the dominant frequency characteristic includes a maximum frequency value, a chirp, a sustained maximum frequency value or a local maximum frequency.

Alternatively or additionally to any of the examples above, the common dominant frequency occurs at a common dominant time point common to the one or more of the plurality of electrodes and identifying a common dominant frequency includes determining an attraction point. Further, the attraction point is defined when the common dominant frequency characteristic, the common dominant frequency and the common dominant time point are substantially equivalent.

Alternatively or additionally to any of the examples above, creating a visual display includes creating a phase map.

Alternatively or additionally to any of the examples above the visual display includes a movie displayed on an anatomical chamber.

Alternatively or additionally to any of the examples above, the phase map displays one or more sinusoids corresponding to the plurality of signals or derivatives thereof.

An example method for mapping the electrical activity of the heart includes collecting a first signal corresponding to the first electrode and a second signal corresponding to the second electrode. Further, collecting the first and second signals occurs over a time period and the first and second signals are collected with a catheter having a plurality of electrodes. The method further includes generating a first time-frequency distribution corresponding to the first signal, identifying a first dominant frequency value occurring at a first dominant frequency and a first time point, generating a second time-frequency distribution corresponding to the second signal, identifying a second dominant frequency value occurring at a second dominant frequency and a second time point and determining an attraction point. The attraction point is defined when the first dominant frequency value substantially relates to the second dominant frequency value.

The above summary of some embodiments is not intended to describe each disclosed embodiment or every implementation of the present disclosure. The Figures, and Detailed Description, which follow, more particularly exemplify these embodiments.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The disclosure may be more completely understood in consideration of the following detailed description in connection with the accompanying drawings, in which.

Figure 1:
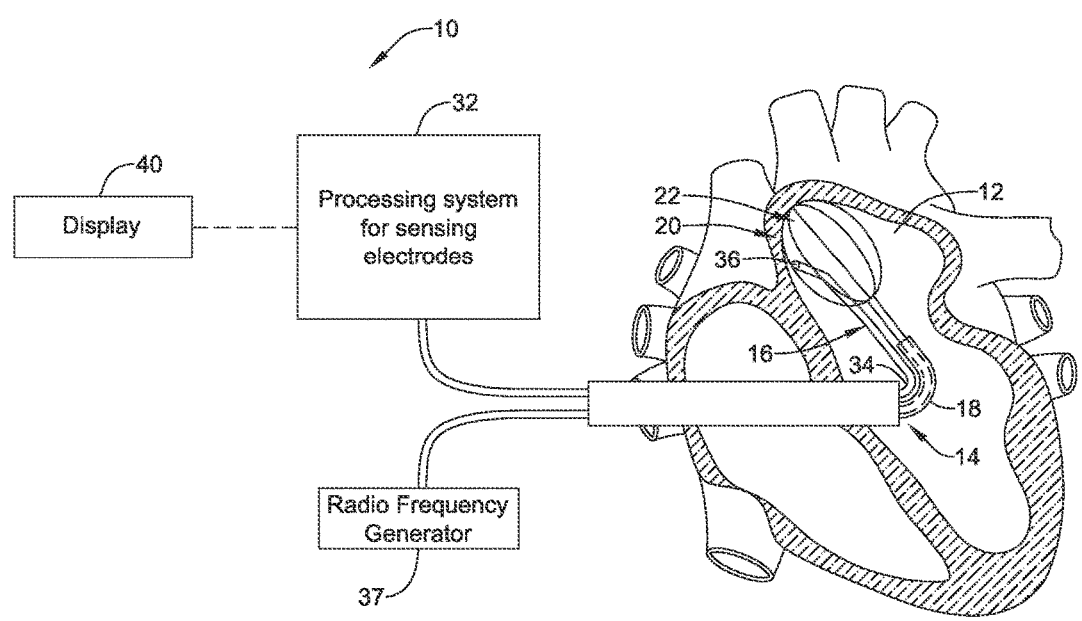
FIG. 1 is a schematic view of an example catheter system for accessing a targeted tissue region in the body for diagnostic and therapeutic purposes.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an example", "some examples", "other examples", etc., indicate that the example described may include one or more particular features, structures, and/or characteristics. However, such recitations do not necessarily mean that all examples include the particular features, structures, and/or characteristics. Additionally, when particular features, structures, and/or characteristics are described in connection with one example, it should be understood that such features, structures, and/or characteristics may also be used in connection with other examples whether or not explicitly described unless clearly stated to the contrary. Also, when particular features, structures, and/or characteristics are described in connection with one example, it is implicit that other examples may include less than all of the disclosed features, structures, and/or characteristics in all combinations.

The following detailed description should be read with reference to the drawings in which similar elements in different drawings are numbered the same. The drawings, which are not necessarily to scale, depict illustrative embodiments and are not intended to limit the scope of the disclosure.

Mapping the electrophysiology of heart rhythm disorders often involves the introduction of a basket catheter (e.g. Boston Scientific Constellation catheter) or other mapping/sensing device having a plurality of sensors into a cardiac chamber. The sensors, for example electrodes, detect physiological signals, such as cardiac electrical activity, at sensor locations. It may be desirable to have detected cardiac electrical activity processed into electrogram signals that accurately represent cellular excitation through cardiac tissue relative to the sensor locations. A processing system may then analyze and output the signal to a display device. Further, the processing system may output the signal as processed output, such as a static or dynamic activation map. A user, such as a physician, may use the processed output to perform a diagnostic procedure.

FIG. 1 is a schematic view of a system 10 for accessing a targeted tissue region in the body for diagnostic and/or therapeutic purposes. FIG. 1 generally shows the system 10 deployed in the left atrium of the heart. Alternatively, system 10 can be deployed in other regions of the heart, such as the left ventricle, right atrium, or right ventricle. While the illustrated embodiment shows system 10 being used for ablating myocardial tissue, system 10 (and the methods described herein) may alternatively be configured for use in other tissue ablation applications, such as procedures for ablating tissue in the prostrate, brain, gall bladder, uterus, nerves, blood vessels and other regions of the body, including in systems that are not necessarily catheter-based.

System 10 includes a mapping catheter or probe 14 and an ablation catheter or probe 16. Each probe 14/16 may be separately introduced into the selected heart region 12 through a vein or artery (e.g., the femoral vein or artery) using a suitable percutaneous access technique. Alternatively, mapping probe 14 and ablation probe 16 can be assembled in an integrated structure for simultaneous introduction and deployment in the heart region 12.

Mapping probe 14 may include flexible catheter body 18. The distal end of catheter body 18 carries three-dimensional multiple electrode structure 20. In the illustrated embodiment, structure 20 takes the form of a basket defining an open interior space 22 (see FIG. 2), although other multiple electrode structures could be used. Structure 20 carries a plurality of mapping electrodes 24 (not explicitly shown on FIG. 1, but shown on FIG. 2) each having an electrode location on structure 20 and a conductive member. Each electrode 24 may be configured to sense or detect intrinsic physiological activity, for example represented as electrical signals, in an anatomical region adjacent to each electrode 24.

In addition, electrodes 24 may be configured to detect activation signals of the intrinsic physiological activity within the anatomical structure. For example, intrinsic cardiac electrical activity may comprise repeating or semi-repeating waves of electrical activity with relatively large spikes in activity at the beginning of activation events. Electrodes 24 may sense such activation events and the times at which such activation events occur. Generally, electrodes 24 may sense activation events at different times as an electrical activity wave propagates through the heart. For instance, an electrical wave may begin near a first group of electrodes 24, which may sense an activation event at relatively the same time or within a relatively small window of time. As the electrical wave propagates through the heart, a second group of electrodes 24 may sense the activation event of the electrical wave at times later than the first group of electrodes 24.

Electrodes 24 are electrically coupled to processing system 32. A signal wire (not shown) may be electrically coupled to each electrode 24 on structure 20. The signal wires may extend through body 18 of probe 14 and electrically couple each electrode 24 to an input of processing system 32. Electrodes 24 sense cardiac electrical activity in the anatomical region, e.g., myocardial tissue, adjacent to their physical location within the heart. The sensed cardiac electrical activity (e.g., electrical signals generated by the heart which may include activation signals) may be processed by processing system 32 to assist a user, for example a physician, by generating processed output—e.g. an anatomical map (e.g., a vector field map, an activation time map) or a Hilbert transform diagram—to identify one or more sites within the heart appropriate for a diagnostic and/or treatment procedure, such as an ablation procedure. For example, processing system 32 may identify a near-field signal component (e.g., activation signals originating from cellular tissue adjacent to mapping electrodes 24) or an obstructive far-field signal component (e.g., activation signals originating from non-adjacent tissue). In such examples where structure 20 is disposed in an atrium of the heart, as in FIG. 1, the near-field signal component may include activation signals originating from atrial myocardial tissue whereas the far-field signal component may include activation signals originating from ventricular myocardial tissue. The near-field activation signal component may be further analyzed to find the presence of a pathology and to determine a location suitable for ablation for treatment of the pathology (e.g., ablation therapy).

Processing system 32 may include dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired physiological activity. In some examples, processing system 32 includes a general purpose microprocessor and/or a specialized microprocessor (e.g., a digital signal processor, or DSP, which may be optimized for processing activation signals) that executes instructions to receive, analyze and display information associated with the received physiological activity. In such examples, processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that processing system 32 can take any suitable form for receiving electrical signals and processing the received electrical signals.

In addition, processing system 32 may be configured to measure the sensed cardiac electrical activity in the myocardial tissue adjacent to electrodes 24. For example, processing system 32 may be configured to detect cardiac electrical activity associated with a dominant rotor or divergent activation pattern in the anatomical feature being mapped. Dominant rotors and/or divergent activation patterns may have a role in the initiation and maintenance of atrial fibrillation, and ablation of the rotor path, rotor core, and/or divergent foci may be effective in terminating the atrial fibrillation. Processing system 32 processes the sensed cardiac electrical activity to generate a display of relevant characteristics. Such processed output may include isochronal maps, activation time maps, phase maps, action potential duration (APD) maps, Hilbert transform diagrams, vector field maps, contour maps, reliability maps, electrograms, cardiac action potentials and the like. The relevant characteristics may assist a user to identify a site suitable for ablation therapy.

Ablation probe 16 includes flexible catheter body 34 that carries one or more ablation electrodes 36. The one or more ablation electrodes 36 are electrically connected to radio frequency (RF) generator 37 that is configured to deliver ablation energy to the one or more ablation electrodes 36. Ablation probe 16 may be movable with respect to the anatomical feature to be treated, as well as structure 20. Ablation probe 16 may be positionable between or adjacent to electrodes 24 of structure 20 as the one or more ablation electrodes 36 are positioned with respect to the tissue to be treated.

Processing system 32 may output data to a suitable device, for example display device 40, which may display relevant information for a user. In some examples, device 40 is a CRT, LED, or other type of display, or a printer. Device 40 presents the relevant characteristics in a format useful to the user. In addition, processing system 32 may generate position-identifying output for display on device 40 that aids the user in guiding ablation electrode(s) 36 into contact with tissue at the site identified for ablation.

Figure 2:
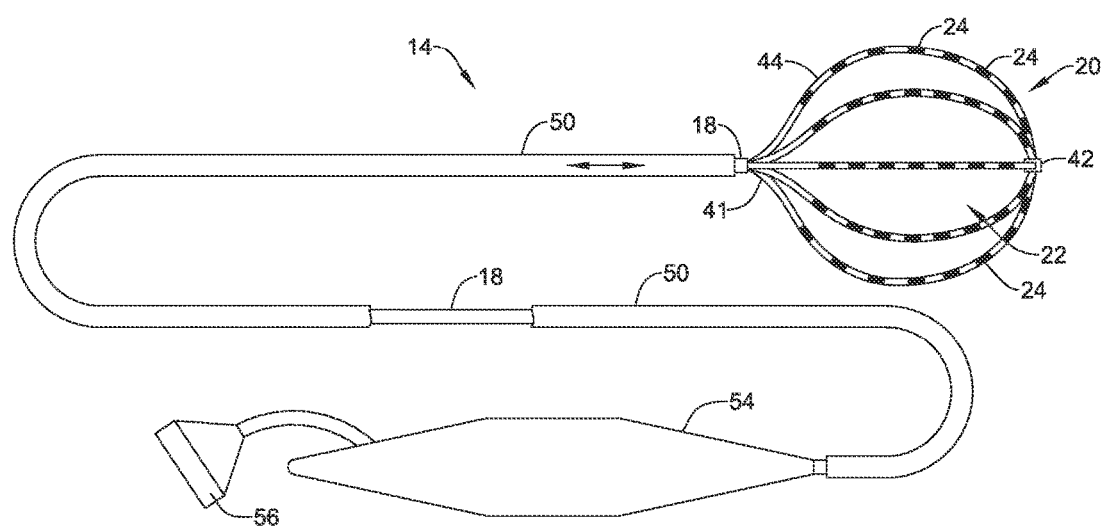
FIG. 2 is a schematic view of an example mapping catheter having a basket functional element carrying structure for use in association with the system of FIG. 1.

FIG. 2 illustrates mapping catheter 14 and shows electrodes 24 at the distal end suitable for use in system 10 shown in FIG. 1. Mapping catheter 14 may include flexible catheter body 18, the distal end of which may carry three-dimensional multiple electrode structure 20 with mapping electrodes or sensors 24. Mapping electrodes 24 may sense cardiac electrical activity, including activation signals, in the myocardial tissue. The sensed cardiac electrical activity may be processed by the processing system 32 to assist a user in identifying the site or sites having a heart rhythm disorder or other myocardial pathology via generated and displayed relevant characteristics. This information can then be used to determine an appropriate location for applying appropriate therapy, such as ablation, to the identified sites, and to navigate the one or more ablation electrodes 36 to the identified sites.

The illustrated three-dimensional multiple electrode structure 20 comprises base member 41 and end cap 42 between which flexible splines 44 generally extend in a circumferentially spaced relationship. As discussed herein, structure 20 may take the form of a basket defining an open interior space 22. In some examples, the splines 44 are made of a resilient inert material, such as Nitinol, other metals, silicone rubber, suitable polymers, or the like and are connected between base member 41 and end cap 42 in a resilient, pretensioned condition, to bend and conform to the tissue surface they contact. In the example illustrated in FIG. 2, eight splines 44 form three-dimensional multiple electrode structure 20. Additional or fewer splines 44 could be used in other examples. As illustrated, each spline 44 carries eight mapping electrodes 24. Additional or fewer mapping electrodes 24 could be disposed on each spline 44 in other examples of three-dimensional multiple electrode structure 20. In the example illustrated in FIG. 2, structure 20 is relatively small (e.g., 40 mm or less in diameter). In alternative examples, structure 20 is even smaller or larger (e.g., less than or greater than 40 mm in diameter).

Slidable sheath 50 may be movable along the major axis of catheter body 18. Moving sheath 50 distally relative to catheter body 18 may cause sheath 50 to move over structure 20, thereby collapsing structure 20 into a compact, low profile condition suitable for introduction into and/or removal from an interior space of an anatomical structure, such as, for example, the heart. In contrast, moving sheath 50 proximally relative to the catheter body may expose structure 20, allowing structure 20 to elastically expand and assume the pretensioned position illustrated in FIG. 2.

A signal wire (not shown) may be electrically coupled to each mapping electrode 24. The signal wires may extend through body 18 of mapping catheter 20 (or otherwise through and/or along body 18) into handle 54, in which they are coupled to external connector 56, which may be a multiple pin connector. Connector 56 electrically couples mapping electrodes 24 to processing system 32. It should be understood that these descriptions are just examples. Some addition details regarding these and other example mapping systems and methods for processing signals generated by a mapping catheter can be found in U.S. Pat. Nos. 6,070,094, 6,233,491, and 6,735,465, the disclosures of which are hereby expressly incorporated herein by reference.

Figure 3:
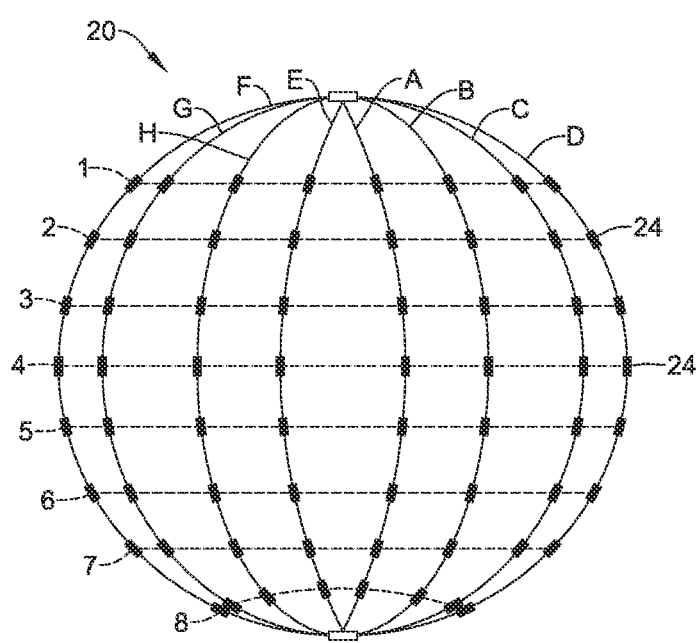
FIG. 3 is a schematic view of an example functional element including a plurality of mapping electrodes.

To illustrate the operation of system 10, FIG. 3 is a schematic side view of an example of basket structure 20 including a plurality of mapping electrodes 24. In the illustrated example, the basket structure includes 64 mapping electrodes 24. Mapping electrodes 24 are disposed in groups of eight electrodes (labeled 1, 2, 3, 4, 5, 6, 7, and 8) on each of eight splines (labeled A, B, C, D, E, F, G, and H). While an arrangement of sixty-four mapping electrodes 24 is shown disposed on basket structure 20, mapping electrodes 24 may alternatively be arranged in different numbers (more or fewer splines and/or electrodes), on different structures, and/or in different positions. In addition, multiple basket structures can be deployed in the same or different anatomical structures to simultaneously obtain signals from different anatomical structures.

After basket structure 20 is positioned adjacent to the anatomical structure to be treated (e.g. left atrium, left ventricle, right atrium, or right ventricle of the heart), processing system 32 may be configured to record the cardiac electrical activity from each electrode 24 channel. Further, the recorded cardiac electrical activity may be related to the physiological activity of the adjacent anatomical structure. For instance, cardiac electrical activity sensed by electrodes 24 may include activation signals which may indicate an onset of physiological activity (e.g. contraction of the heart). Further, cardiac electrical activity corresponding to physiological activity may be sensed in response to intrinsic physiological activity (e.g. intrinsically generated electrical signals) or based on a predetermined pacing protocol instituted by at least one of the plurality of electrodes 24 (e.g. delivered electrical signals delivered by a pacing device).

It should be noted that while much of the discussion herein relates to the use of system 10 within the heart, in some instances system 10 may be utilized in other areas of the body in addition to computed, simulated and/or theoretical computations. For example, embodiments may be applied to neurological activity, endocardial and/or epicardial activity, unipolar measurements, bipolar measurements, both unipolar and bipolar measurements, or the like. In other words, the disclosed embodiments and/or techniques may be applied to any electrical measurement and/or any electrical activity, real or computed.

The arrangement, size, spacing and location of electrodes along a constellation catheter or other mapping/sensing device, in combination with the specific geometry of the targeted anatomical structure, may contribute to the ability (or inability) of electrodes 24 to sense, measure, collect and transmit electrical activity of cellular tissue. As stated, because splines 44 of a mapping catheter, constellation catheter or other similar sensing device are bendable, they may conform to a specific anatomical region in a variety of shapes and/or configurations. Further, at any given position in the anatomical region, structure 20 may be manipulated such that one or more splines 44 may not contact adjacent cellular tissue. For example, splines 44 may twist, bend, or lie atop one another, thereby separating splines 44 from nearby cellular tissue. Additionally, because electrodes 24 are disposed on one or more of splines 44, they also may not maintain contact with adjacent cellular tissue. Electrodes 24 that do not maintain contact with cellular tissue may be incapable of sensing, detecting, measuring, collecting and/or transmitting electrical activity information. Further, because electrodes 24 may be incapable of sensing, detecting, measuring, collecting and/or transmitting electrical activity information, processing system 32 may be incapable of accurately displaying diagnostic information and/or processed output. For example, some necessary information may be missing and/or displayed inaccurately.

In addition to that stated above, electrodes 24 may not be in contact with adjacent cellular tissue for other reasons. For example, manipulation of mapping catheter 14 may result in movement of electrodes 24, thereby creating poor electrode-to-tissue contact. Further, electrodes 24 may be positioned adjacent fibrous, dead or functionally refractory tissue. Electrodes 24 positioned adjacent fibrous, dead or functionally refractory tissue may not be able to sense changes in electrical potential because fibrous, dead or functionally refractory tissue may be incapable of depolarizing and/or responding to changes in electrical potential. Finally, far-field ventricular events and electrical line noise may distort measurement of tissue activity.

However, electrodes 24 that contact healthy, responsive cellular tissue may sense a change in the voltage potential of a propagating cellular activation wavefront. The change in voltage potential of cellular tissue may be sensed, collected and displayed as an electrogram. An electrogram may be a visual representation of the change in voltage potential of the cellular tissue over time. Additionally, it may be desirable to define a specific characteristic of an electrogram as a "fiducial" point of the electrical signal. For purposes of this disclosure, a fiducial point may be understood as a characteristic of an electrogram that can be utilized as an identifying characteristic of cellular activation. Fiducial points may correspond to the peak magnitude, change in slope, and/or deflection of the electrical signal. It is contemplated that fiducial points may include other characteristics of an electrogram or other signal used to generate diagnostic and/or processed output. Further, fiducial points may be identified manually by a clinician and/or automatically by processing system 32.

An electrogram representing a change in voltage potential over time may be defined as visually displaying the electrical signal in the "time domain." However, it is generally understood that any electrical signal has a corollary representation in the "frequency domain." Transforms (e.g. Fourier, Fast Fourier, Wavelet, Wigner-Ville) may be utilized to transform signals between the time domain and frequency domain, as desired. Electrical signals also have a corollary representation in the analytic domain which can be obtained through transforms such as the Hilbert transform.

Further, in a normal functioning heart, electrical discharge of the myocardial cells may occur in a systematic, linear fashion. Therefore, detection of non-linear propagation of the cellular excitation wavefront may be indicative of cellular firing in an abnormal fashion. For example, cellular firing in a rotating pattern may indicate the presence of dominant rotors and/or divergent activation patterns. Further, because the presence of the abnormal cellular firing may occur over localized target tissue regions, it is possible that electrical activity may change form, strength or direction when propagating around, within, among or adjacent to diseased or abnormal cellular tissue. Identification of these localized areas of diseased or abnormal tissue may provide a user with a location for which to perform a therapeutic and/or diagnostic procedure. For example, identification of an area including reentrant or rotor currents may be indicative of an area of diseased or abnormal cellular tissue. The diseased or abnormal cellular tissue may be targeted for an ablative procedure. Various processed outputs, such as those described above, may be used to identify areas of circular, adherent, rotor or other abnormal cellular excitation wavefront propagation.

Figure 4:
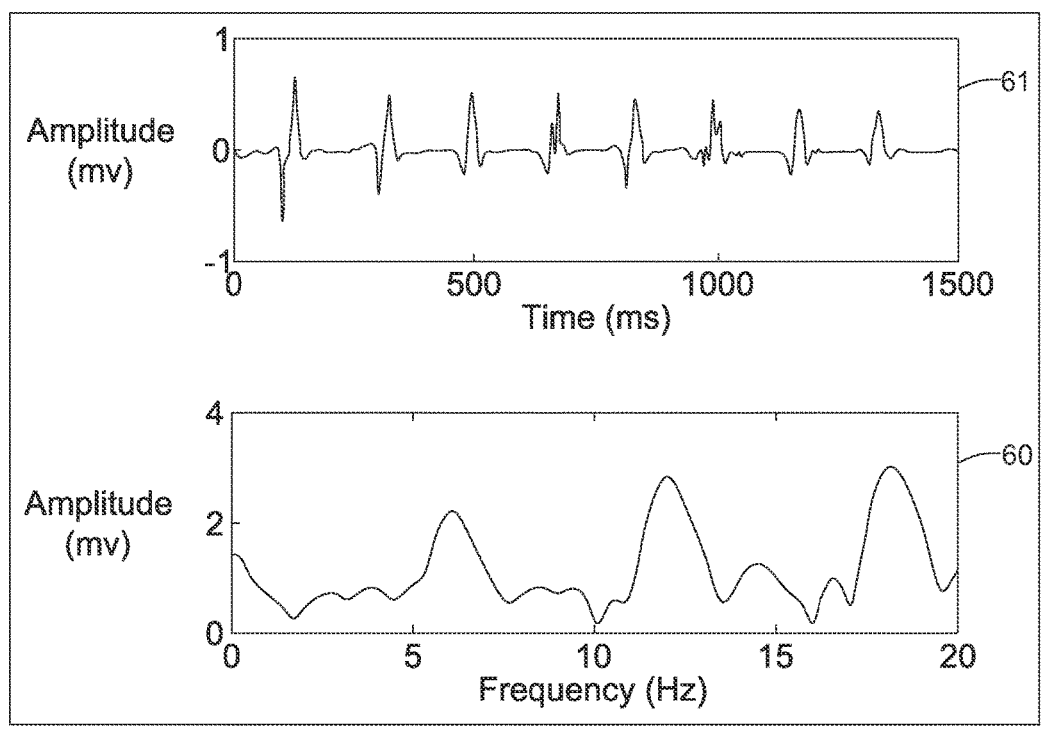
FIG. 4 is an illustration of an example electrogram signal in the time domain and a corresponding frequency representation in the frequency domain.

In at least some embodiments, the process of generating processed output may begin by collecting signals (e.g. a first signal corresponding to the first electrode and a second signal corresponding to the second electrode) from one or more of sixty-four electrodes 24 on structure 20. As stated above, the sensed signals may be collected and displayed in the time domain. However, in at least one embodiment, signals displayed in the time domain may be transformed into the frequency domain to further generate processed output. As stated above, transforms such as the Fourier Transform, Fast Fourier Transform, or any other transform that produces frequency and power information for a signal may be utilized to transform signals between the time and frequency domains. FIG. 4 illustrates an example electrogram signal in the time domain 60 along with its corresponding frequency representation in the frequency domain 62.

Additionally, in some instances it may be desirable to analyze frequency representations over a time interval. For example, it may be desirable to analyze collected signal data as a time-frequency representation. In some instances, a time-frequency representation may be referred to as a spectrogram. For purposes of this disclosure, the terms time-frequency representation and spectrogram are used interchangeably.

Figure 5:
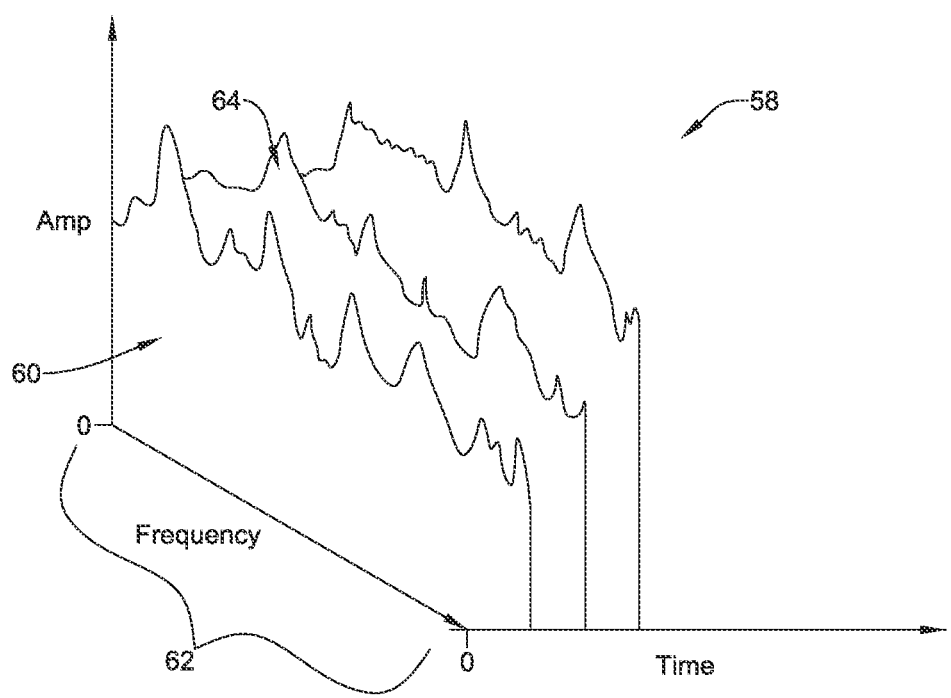
FIG. 5 is an illustration of an example time-frequency representation for a single electrode.

A spectrogram may represent the magnitude of frequencies corresponding to cellular tissue response as it varies with time (or another variable). In some instances, transforms such as the Fourier Transform, Short-Time Fourier Transform, Wavelet transform, or any other transform that produces frequency and power information for a signal may be utilized to generate a spectrogram. FIG. 5 shows a three-dimensional visual representation of example spectrogram 58. Spectrogram 58 may correspond to an example electrode 24 on multiple electrode structure 20. It should be understood that while spectrogram 58 is displayed visually in FIG. 5, processing system 32 may generate the data necessary to reconstruct a spectrogram without actually creating a visual display of the spectrogram. Further, processing system 32 may utilize the collected data independent of visually displaying a spectrogram.

As shown in FIG. 5, the spectrogram may display a frequency spectrum 60 which varies in magnitude over a range of frequencies 62. In practice, frequency range 62 may correspond to frequencies included in the original, collected electrical signals and/or a frequency range selected by a user. Additionally, processing system 32 may select a range of frequencies for which data is utilized from one or more of the signals collected from the sixty-four electrodes 24 on structure 20. For example, a frequency range of 3-7 Hz has been shown (empirically) to be a frequency range in which abnormal cardiac electrical activity occurs. For example, atrial fibrillation may occur predominantly in the frequency range of 3-7 Hz. It is contemplated that other abnormal atrial events may also occur within this frequency range. However, it should be understood that abnormal cardiac activity may occur in frequency ranges other than 3-7 Hz.

Additionally, it should be understood that the selected and/or filtered frequency range may be greater or less than 3-7 Hz (e.g. each limit could be modified by ±2-10 Hz). Selecting or ignoring data within a particular frequency range (e.g. in accordance with the range expected for a certain application) may improve the techniques and/or processed output of the embodiments disclosed herein. For example, the frequency range may be a narrower range (e.g. 3-7 Hz, 2-10 Hz, 5-20 Hz), or may be a larger range (e.g. 0-60 Hz, 5-100 Hz, 0-200 Hz).

As shown in FIG. 5, frequency spectrum 60 may correspond to a portion of the time interval over which original electrical signals were sensed and collected. Further, a frequency spectrum may change over the time interval. For example, a second frequency spectrum 64 may occur at a second time interval (as compared to the time interval corresponding to frequency spectrum 62). As shown, frequency spectrum 64 may be different from frequency spectrum 60. The difference between frequency spectrum 64 and frequency spectrum 60 may be due to a change in the magnitude of the spectrum with respect to frequency values over time. Further, the change in magnitude of the spectrum with respect to frequency values over time may correspond to a changing cellular tissue response underlying the original sensed and collected electrical signals.

Figure 6:
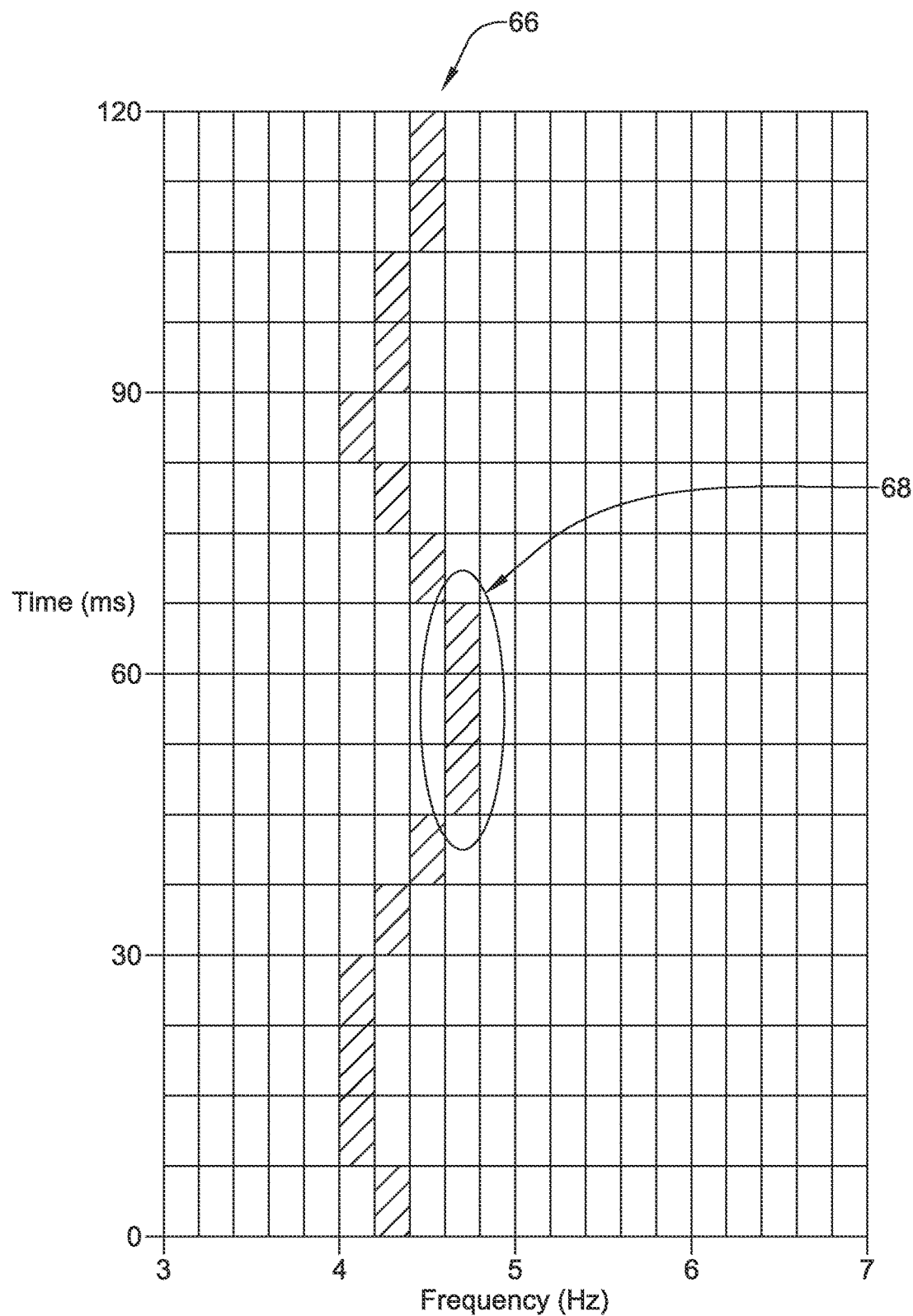
FIG. 6 is an illustration of an example two-dimensional time-frequency representation for a single electrode.

In addition to that displayed in FIG. 5, a two-dimensional spectrogram 66 is shown in FIG. 6. As shown in FIG. 6, spectrogram 66 may convey the same information as spectrogram 58. However, the information may be presented in a different format. For example, in FIG. 6, the time interval may be displayed on the Y-axis, while the frequency range may be displayed on the X-axis. Further, the magnitude values for each frequency may be conveyed visually. For example, the magnitude values may be conveyed by a color spectrum. In other words, a range of colors may indicate the relative magnitude of a given frequency. The example disclosed herein is merely illustrative—other methods for displaying the spectrogram (including frequency variability over time) and/or the magnitude of a given frequency are contemplated. For example, magnitude values may be indicated by texture.

In some instances, electrical signals sensed and collected by electrodes 24 may exhibit the same or very similar frequency characteristics over a given time interval. For example, electrical signals sensed and collected by electrodes 24 may exhibit the same or similar magnitudes at a given frequency over a given time interval. In other words, a given electrode may sense and collect electrical signals that exhibit a consistent magnitude at a given frequency over an interval of time. Further, similar frequency characteristics may be displayed, reproduced and/or identified on a spectrogram. For example, a spectrogram may convey magnitude values that are consistent at a given frequency over an interval of time.

FIG. 6 shows example spectrogram 66 displaying a time interval in which magnitude values are consistent at a given frequency and/or range of frequencies. For example, a frequency at which magnitude values are consistent at a given frequency and over a time interval is identified by bolded circle 68. In this example, bolded circle 68 shows magnitude values that are substantially equivalent to one another (as indicated by the consistent cross-hatching) at the same frequency over a given time interval. It can be seen in FIG. 6 that the example frequency (indicated by bolded circle 68) at which the magnitude values are substantially equivalent is approximately 4.7 Hz. Further, the magnitude values occur over an approximate time interval of 45 ms to 67.5 ms. It is contemplated that in some instances the magnitude values may not be consistent across a given frequency or time interval.

As stated above, the magnitude values may remain consistent at a single frequency or across a range of frequencies. As illustrated in FIG. 6, the frequency magnitudes remain consistent over a frequency range of approximately 4 to 5 Hz. In some instances, a single frequency at which magnitude values remain substantially consistent may be referred to as the "dominant frequency." Similarly, a frequency band at which magnitude values remain substantially consistent may be referred to as a "dominant frequency band." For example, in FIG. 6, 4.5 Hz may be considered a dominant frequency. Similarly, 4-5 Hz may be considered a dominant frequency band. It is understood that more than one dominant frequency and/or dominant frequency band may be present in a given spectrogram.

Further, it should be understood that the embodiments described above may be applicable to one or more of electrodes 24 on multiple electrode structure 20. For example, in some instances it may be desirable to generate a spectrogram for one or more of electrodes 24 on multiple electrode structure 20. Further, it may be desirable to compare the information provided by the spectrograms generated for one or more of electrodes 24 on multiple electrode structure 20. For example, it may be desirable to compare and/or correlate the magnitude, dominant frequency, dominant frequency band and/or the time point or time interval at which the magnitude, dominant frequency and/or dominant frequency band occur across one or more electrodes 24 on multiple electrode structure 20.

In some embodiments it may be desirable to identify and compare and/or correlate a unique spectrogram "characteristic" for a single electrode 24 with the spectrograms of the remaining electrodes 24 on multiple electrode structure 20. In some instances a unique spectrogram characteristic may be referred to as a "mode." It is contemplated that a variety of characteristics/modes may be used to compare the spectrograms of electrodes 24 on multiple electrode structure 20. For example, the specific characteristic/mode may be a frequency value having a maximum magnitude (herein called a "maximum frequency value"), a chirp, a sustained frequency value having a maximum magnitude (herein called a "sustained maximum frequency value"), a local frequency value having a maximum magnitude (herein called a "local maximum frequency value") and/or other dominant frequency characteristics. These are just examples. Other characteristics/modes are contemplated. In some instances, the mode may be referred to as a "dominant characteristic." The dominant characteristic may occur at a frequency referred to as a "dominant frequency" and at a time point referred to as a "dominant time point." In some instances, the value (e.g. power, amplitude) of a dominant characteristic occurring at a frequency referred to as a "dominant frequency" and at a time point referred to as a "dominant time point" may be referred to as a "dominant frequency values" and/or a "dominant frequency value representation." Further, in some instances the mode may be referred to as a "dominant frequency value." Additionally, it is contemplated that other user-defined dominant frequency values may be defined as modes. In some instances a single spectrogram for a single electrode may exhibit one or more modes identified by processing system 32.

In some instances processing system 32 may group electrodes that exhibit a particular characteristic. Further, processing system 32 may selectively group electrodes exhibiting a particular characteristic only when the common characteristic occurs at substantially the same frequency and at substantially the same time point and/or time interval. In other words, processing system 32 may selectively group electrodes exhibiting a particular characteristic when the particular characteristics of the individual electrodes substantially relate to one another. For example, in some instances the characteristic used to group electrodes may be a maximum magnitude occurring at a particular frequency. A maximum magnitude occurring at a particular frequency The maximum magnitude occurring at that particular frequency may occur at a single time point or may occur over a time interval. As stated above, the characteristic utilized to group electrodes may be a frequency value having a maximum magnitude (herein called a "maximum frequency value"), a chirp, a sustained frequency value having a maximum magnitude (herein called a "sustained maximum frequency value"), a local frequency value having a maximum magnitude (herein called a "local maximum frequency value") and/or other dominant frequency characteristic present on a given spectrogram for any electrode 24.

In some instances, processing system 32 may selectively group electrodes that exhibit a particular common characteristic occurring at a common frequency and common time point or time interval. In other words, processing system 32 may initially analyze the spectrogram of a given electrode for a particular frequency characteristic (e.g. a sustained frequency value having a maximum magnitude, etc.). Once processing system 32 identifies the frequency characteristic, processing system 32 may then determine the frequency and the time point at which the frequency characteristic occurred. Having determined the frequency characteristic, the frequency at which the characteristic occurs and the time point at which the characteristic occurs, processing system 32 may analyze the spectrograms of the remaining electrodes 24 in search of a match to the common characteristic, common frequency and common time point of the initial electrode. Electrodes having spectrograms exhibiting the common characteristic, frequency and time point may then be grouped together. A common characteristic, frequency and time point may be referred to as an "attraction point." Additionally, the grouping of electrodes having spectrograms that exhibit the characteristic, frequency and time point may be referred to as an "attraction point."

In addition, it should be understood that a single spectrogram from a given electrode may exhibit one or more characteristics and/or dominant frequency values over the time interval of the spectrogram. In other words, different types of identifiable characteristics (e.g. maximum frequency value, a chirp, sustained maximum frequency value, a local maximum frequency value and/or other dominant frequency characteristic present on a given spectrogram for any electrode 24) may occur at different frequencies and at different time points. Processing system 32 may analyze, compare, correlate, match and/or group one or more of the characteristics among one or more of all electrodes 24. Further, the matching characteristics may result in one or more different attraction points and resulting modes. In some instances, a mode may define an electrical activation pattern. Further, in some instances one or more modes of electrical activation patterns may be defined by and/or include one or more attraction points. Additionally, the modes of electrical activation patterns may correspond to one or more anatomical features.

Figure 7:
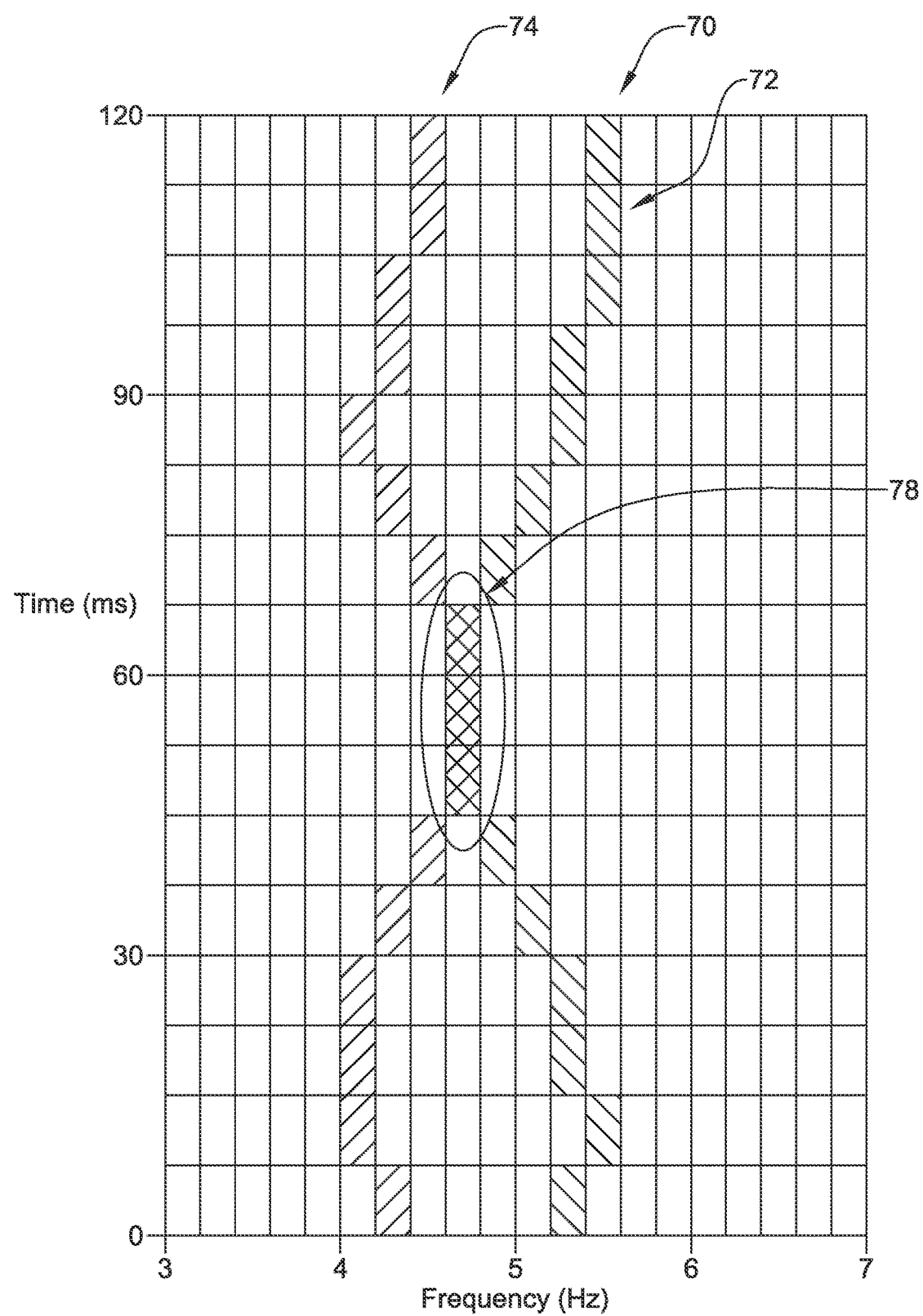
FIG. 7 is an illustration of an example two-dimensional time-frequency representation for two electrodes.

FIG. 7 shows example spectrogram 70 displaying maximum magnitude values 72, 74 for two example electrodes. For illustrative purposes, it should be understood that the characteristic being identified on spectrogram 70 for each electrode is maximum magnitude. However, the characteristic may be a maximum frequency value, a chirp, sustained maximum frequency value, a local maximum frequency value and/or other dominant frequency characteristic present on a given spectrogram for any electrode 24.

As shown in FIG. 7, the maximum magnitude values 72, 74 (and frequency and time point at which they occur) are identified by the left and right diagonal cross-hatching shown. Further, bolded circle 78 illustrates a frequency and time interval for which the maximum magnitude values 72, 74 of both electrodes substantially match (as indicated by the common cross-hatching). In other words, bolded circle 78 illustrates that the individual electrodes exhibiting the maximum magnitude values 72, 74 share a common magnitude at a common frequency over a common time point. As stated above, this particular combination may be referred to as an attraction point. Further, the electrodes exhibiting maximum magnitude values 72, 74 may sustain the same mode over this particular time interval. It should be understood that, in practice, electrodes exhibiting a particular mode may often be related spatially on multiple electrode structure 20. Therefore, in some instances, identification of particular electrode modes may provide a specific spatial location for the application of targeted therapy. The mode and corresponding location information may also inform a best therapy to apply or eliminate therapy alternatives that may be ineffective for a given circumstance. The therapy may include ablation therapy, pharmaceutical therapy, stimulation therapy, or the like.

It should be understood that while some embodiments described above may determine attraction points as they relate to common characteristics occurring at common frequencies over a common time interval, other embodiments may contemplate that attraction points may be defined as a particular characteristic occurring at a single frequency and at a single point in time.

Additionally, the method by which frequency characteristics are defined may vary according to a number of different factors. For example, a particular frequency characteristic may include a threshold value that must be met in order for processing system 32 to use that particular characteristic when searching for attraction points among the spectrograms of electrodes 24. In some embodiments including a frequency characteristic associated with spectral magnitude, the threshold may be a minimum expected magnitude value whereby the characteristic is satisfied when the magnitude value equals or substantially exceeds the threshold value.

As stated above, an attraction point may be defined when a particular characteristic or mode occurring at a particular frequency and time point is commonly shared among a group of spectrograms. Additionally, an attraction point may also be defined not only when a characteristic occurs at a single frequency or time point, but also when a particular characteristic occurs over a range of frequencies or a time interval. For example, in some instances processing system 32 may identify an attraction point between two example electrodes despite the fact that the frequencies at which the common characteristic occurs varies between the two electrodes. Similarly, in some instances processing system 32 may define an attraction point between two example electrodes despite the fact that the time points at which the common characteristic occurs varies between the two electrodes. Additionally, in some instances processing system 32 may define an attraction point between two example electrodes despite the fact that both the frequencies and the time points at which the common characteristic occurs varies between the two electrodes.

In some instances, the embodiments described here may include processing system 32 being preprogrammed to implement, utilize and/or process the steps, methods, calculations and/or algorithms. However, it is understood that any given characteristic, value, threshold, etc. may be user defined. In other words, processing system may be configured to allow input from a user (e.g. clinician) relating to particular characteristics and/or input variables. Allowing user defined input may permit a user to "customize" a particular algorithm or system output.

Figure 8:
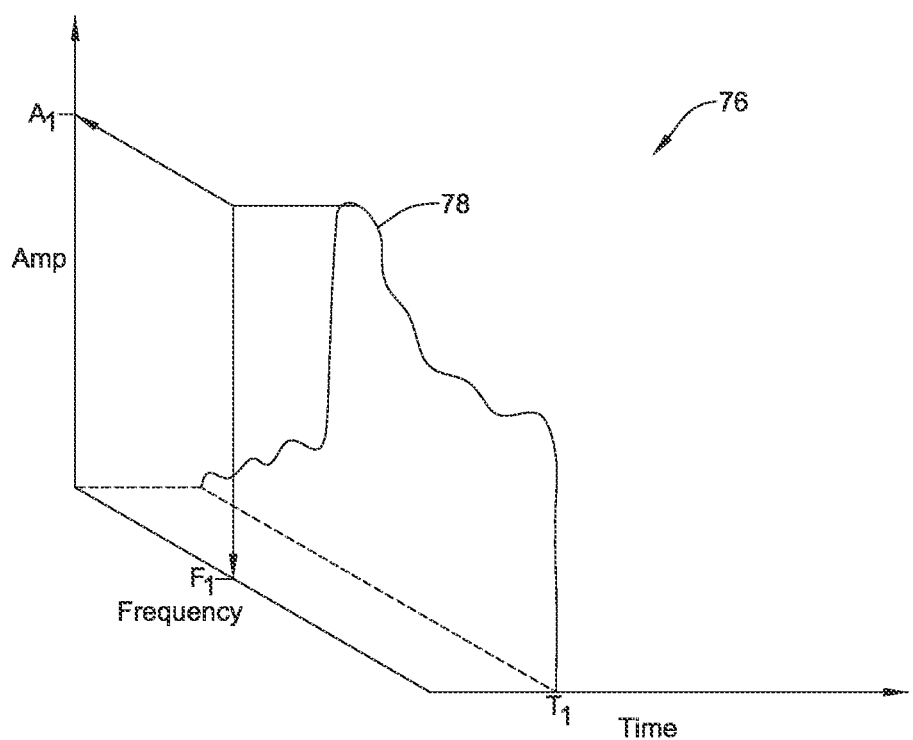
FIG. 8 is an illustration of an example time-frequency representation including a single magnitude peak.

As described above, processing system 32 may seek, target and/or select one or more specifically defined spectrogram characteristics. It is understood that a given spectrogram may include one or more modes. For example, FIG. 8 shows example spectrogram 76 for a single electrode 24. Further, FIG. 8 shows a peak magnitude 78 (corresponding to example magnitude value A1) occurring at frequency F1 and at time point T1. In this illustration, processing system may seek, target and/or select peak magnitude 78 as the characteristic for which to compare and determine attraction points among remaining electrodes 24. Alternatively, spectra from multiple electrodes may be compared to emphasize characteristic features that are common among them. In some instance, a group of electrodes may directly correlate to a particular anatomical feature (e.g. location in a cardiac chamber). Therefore, identifying common spectra characteristics associated with a particular group of electrodes may allow identification of the corresponding anatomical feature.

In some instances, multiple sets of spectrogram characteristics may involve different and/or overlapping groups of electrodes (and therefore, different and/or overlapping anatomical features). These groups of electrodes and corresponding anatomical features may be defined by multiple modes occurring over the same time period. The multiple modes may be independent of each other or dependent on each other (e.g. influence each other) over time. Identification of individual modes and/or the relationship between multiple dependent modes may be assessed from local electrode groups, globally over all electrodes, from individual electrodes and/or from any combination of electrodes as modes are identified and associated with different electrode sub-groups.

Further, a given mode may be "deconstructed" to identify the underlying electrical activity contributing to a particular pathology over a particular epoch of time. For example, a particular spectrogram may exhibit a relatively complex spectral pattern in both frequency and over time (e.g. spectrogram characteristics, modes, etc.). Through a deconstruction process, it may be possible to remove one or more modes from the complex pattern. This may allow identification of a particular pattern, previously unidentifiable, that may correlate to a particular pathology and, thus, can be treated accordingly. In other words, processing techniques may be applied which correlate a particular mode with a particular electrical pattern. For example, processing techniques may be able to determine that a particular mode correlates to a rotor, ectopic electrical activity, etc., with different relative powers over time. These patterns may then be deconstructed into multiple modes over time and targeted by a particular therapy.

In some instances, a particular type of observed pathology (e.g. arrhythmia) may be the result of collaboration between dominant and sub-dominant modes. Understanding the relationship between multiple modes may indicate whether to treat one or more particular electrical patterns (corresponding to the one or more modes).

For example, a given dominant spectral characteristic may (on its face) be recognizable as a targeted mode. In reality, however, the observed spectra characteristic may include two or more sub dominant modes contributing to the electrical pattern over time. Further, the two or more modes (e.g. dominant and sub-dominant) may be influencing the occurrence of one another with different relative powers over time. In this example, it may desirable to identify the presence of the two individual modes and use deconstruction techniques to identify the underlying electrical patterns corresponding to the individual modes. Further, therapy may be tailored to the particular pathology corresponding to each individual mode and electrical pattern.

Figure 9:
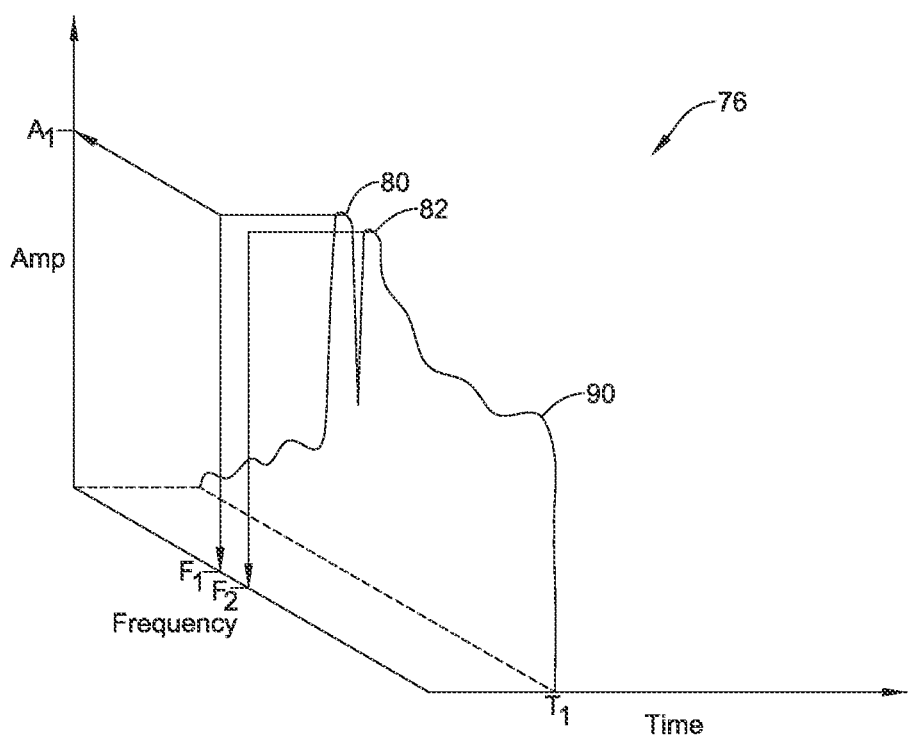
FIG. 9 is an illustration of an example time-frequency representation including dual magnitude peaks.

However, in some instances a spectrogram characteristic (e.g. peak magnitude) may include one or more characteristics for which processing system 32 may not be able to initially identify. For example, FIG. 9 shows example spectrum 76 as described above. However, as can be seen in FIG. 9, peak magnitude 78 (in fact) includes two separate peak magnitude values 80, 82 occurring at example frequencies F1 and F2, respectively. It should be understood that frequencies F1 and F2 may be very close in value, and therefore, indistinguishable by processing system 32 during initial processing steps.

In some instances, it may be desirable for processing system 32 to further refine frequency spectrum signals in order for processing system 32 to select, group and define attraction points accurately. For example, peak magnitude values 80, 82 shown in FIG. 9 may reflect frequency values occurring at frequencies that are derived from two distinct cellular pathologies (e.g. arrhythmias). In that case, it would be inaccurate to group peak magnitude values 80, 82 (and their corresponding frequencies) into the same attraction point and/or mode. Further, the electrode from which spectrogram 76 is derived may be grouped into two different modes corresponding to the two distinct peak frequencies at which the peak frequency values occur. Therefore, to more accurately determine attraction points and/or modes it may be desirable to apply signal processing techniques (e.g. frequency estimate techniques) to refine and/or modify the frequency spectrum signals contributing to a given spectrogram. In some embodiments, the frame of the time-frequency representation may be widened in the time dimension, thus yielding a higher resolution in frequency.

In some embodiments, it may be desirable to utilize the harmonic components of a given frequency spectrum to refine and/or modify the frequency spectrum. For example, it may be possible to incorporate the power values at integer multiples of any base frequency (e.g. dominant frequency, frequency at which a maximum frequency value occurs, etc.). Further, the power values occurring at the integer multiples of the base frequency may be combined with that of the base frequency, thereby producing a modified measure of the relative power or magnitude of the harmonic spectrum as a function of base frequency. This measure is expected to produce a peak at the frequency corresponding to that of the underlying periodicity and in practice may be a modified or refined value of the base frequency.

Additionally, this technique may be utilized for more than one frequency along a frequency spectrum, thereby modifying the frequency values along a portion or the entire frequency spectrum yielding what may be referred to as a "periodicity spectrum." Therefore, this technique may provide differentiation among closely related magnitude frequency peaks. In some embodiments this technique may be referred to as applying a comb filter across a signal, derivative of a signal and/or a frequency spectrum. Additionally, this technique may also be applied across the frequency spectrum for the entire time interval of a given spectrogram, resulting in a time-frequency representation of the periodicity spectrum. In some instances, a comb filter may be applied directly to one or more attraction points.

Figure 10:
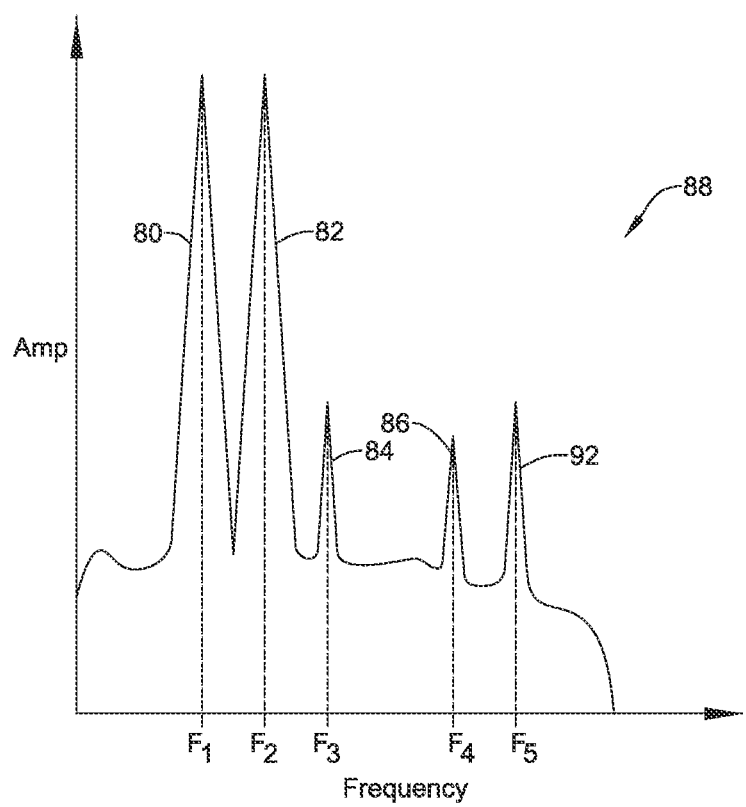
FIG. 10 is an illustration of an example frequency spectrum including dual magnitude peaks.

FIG. 10 shows a two-dimensional representation 88 of the frequency spectrum 90 of FIG. 9, including dual magnitude peaks 80, 82 and harmonic peaks 84, 86 occurring at first integer multiples of magnitude peaks 80,82, respectively. As discussed above, it may be desirable to add the magnitude value 84 occurring at the first integer multiple F3 (e.g. 2*F1) of base frequency F1 (corresponding to peak magnitude 80) to the magnitude value of peak 80. In addition, it may also be desirable to add the magnitude value 86 occurring at the first integer multiple F4 (e.g. 2*F2) of base frequency F2 (corresponding to peak magnitude 82) to the magnitude value of peak 82. It is understood that the magnitude values occurring at the integer multiples may be different, and therefore, adding each of them to their respective base frequency may result in a differentiation of the peak magnitude values for the base frequencies. This example illustrates utilizing the first integer multiples F3, F4 of the base frequencies F1, F2 (e.g. 2*F1, 2*F2). However, it is contemplated that frequency values occurring at additional integer multiples (e.g. 3, 4, 5, 6, 7 etc.) may be added to further differentiate base frequency values. For illustrative purposes, FIG. 10 further displays spurious peak 92 occurring at non-integer multiple F5.

Figure 11:
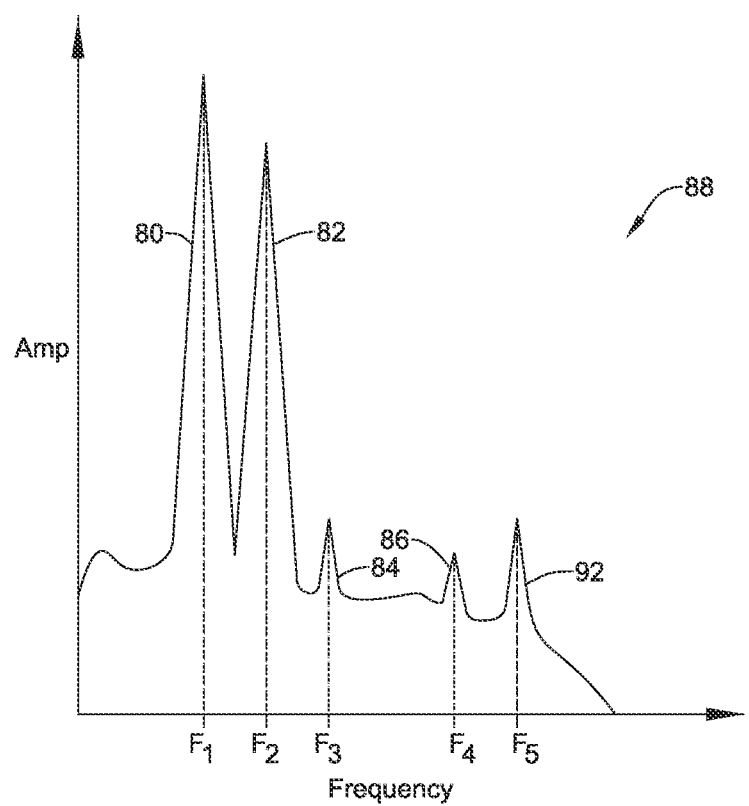
FIG. 11 is an illustration of an example frequency spectrum including dual magnitude peaks having different amplitude values.

FIG. 11 illustrates the differentiation of peak magnitudes 80 and 82 after magnitude values 84 and 86 are added to the base frequency values occurring at frequencies F1 and F2. As can be seen, the magnitude peaks 80 and 82 show vertical separation from one another. This differentiation may allow processing system 32 to identify and group the frequency spectrum characteristics more accurately. Specifically, it may allow processing system 32 to either include or exclude the electrode from which the frequency spectrum 88 was derived from one or more modes.

As illustrated in FIG. 11, after having been added to magnitude peaks 80 and 82, magnitude values 84 and 86 are substantially reduced with respect to both magnitude values 80 and 82 and magnitude values 84 and 86 in FIG. 10. Additionally, relative to magnitude values 80 and 82, the magnitude value of spurious peak 92 (corresponding to non-integer multiple F5) is substantially reduced with respect to its value in FIG. 10. Additionally, relative to magnitude values 80 and 82 (and as illustrated in FIG. 11), the baseline magnitude values surrounding peaks 84, 86 and 92 trend downward (in comparison to the magnitude values shown in FIG. 10) as the frequency increases.

It is contemplated that the harmonic technique (e.g. including the use of a filter such as a comb filter) disclosed herein may be applied before attraction points are identified, after attraction points have been identified or both before and after attraction points have been identified. It is also contemplated that the harmonic technique may be applied to spectra combined from multiple electrodes. Further, it is contemplated that after a harmonic technique is applied and magnitude peaks are differentiated, one or more of the magnitude peaks may be included in an attraction point. Similarly, one or more of the peaks may be excluded from an attraction point.

Additionally, after processing system 32 determines attraction points and/or modes, the processing system 32 may utilize the frequency at which the attraction points and/or modes occur to create a diagnostic display corresponding to the spatial relationship of the electrodes contributing to the attraction points and/or modes.

For example, processing system 32 may determine the sinusoid representation and/or phase value correlated to the dominant frequency of the attraction points and/or modes collected from electrodes 24 on structure 20. For example, the Fourier transform may be used to determine and/or generate a sinusoid and/or phase value for each electrode 24 at the selected frequency (e.g. frequency of the attraction points and/or modes). Alternatively, such a sinusoid model may be estimated for each electrode 24 using estimation methods well-documented in the art of signal processing and apply them to the electrode waveform over the time epoch associated with the attraction point. Further, each derived sinusoid with a corresponding phase offset may be utilized to create a dynamic "movie" or "dynamic map" corresponding to the particular attraction point and/or mode from which the selected frequency was derived. A movie or dynamic map may provide a medium that allows better visualization of wavefront propagation and/or the focal impulse of a particular pathology via a summary characteristic (e.g. activation time, phase, etc). In some embodiments, the visual display (e.g. movie, dynamic map, phase map etc.) may be portrayed on an anatomical representation of a cardiac chamber of interest. Additionally, the visual display (e.g. movie, dynamic map, phase map, etc.) may correspond to the first and/or second dominant frequency values changing over multiple heart beasts and/or over various cardiac regions or chambers. Some additional details regarding creating a dynamic phase map from sinusoid representations can be found in U.S. patent application Ser. No. 61/991,235 titled "Medical Devices for Mapping Cardiac Tissue" the disclosure of which is hereby expressly incorporated herein by reference.

It should be understood that processing system 32 may selectively eliminate some of the collected signals before performing the techniques and/or embodiments disclosed herein. For example, it may be beneficial to eliminate signals collected by electrodes that are not in electrical contact, or in poor electrical contact, with excitable cellular tissue of the heart. Such signals may not provide useful information and can skew results of the above described techniques.

Alternatively, instead of eliminating collected signals that are not providing useful information, processing system 32 may instead interpolate or estimate the value of any signal which is not otherwise providing desirable information. Processing system 32 may utilize the interpolated or estimated data (e.g. signal data) to better calculate, determine or generate useful processed data and/or smooth, refine, or present processed data in a more desirable manner.

It is contemplated that any of the disclosed methods may be implemented across multiple beats, excitations or cardiac pacing time intervals. Further, data collected over multiple heart beats and/or excitations may be analyzed using statistical methodologies and applied to the disclosed methods. For example, activation times may be collected over a series of heart beats and/or pulses. A statistical distribution of the collected activation times may be calculated, analyzed and incorporated into disclosed methods.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A system for mapping the electrical activity of the heart, the system comprising:
    a catheter shaft, wherein a plurality of electrodes is coupled thereto, and wherein the plurality of electrodes includes a first electrode and a second electrode;
    a processor, wherein the processor is configured to:
        receive a first signal corresponding to the first electrode and a second signal corresponding to the second electrode, wherein collecting the first and second signals occurs over a time period;
        generate a first time-frequency distribution corresponding to the first signal;
        identify a first dominant frequency value occurring at a first dominant frequency and a first time point;
        generate a second time-frequency distribution corresponding to the second signal;
        identify a second dominant frequency value occurring at a second dominant frequency and a second time point;
        determine an attraction point, wherein the attraction point is defined when the first dominant frequency value substantially relates to the second dominant frequency value;
        identify a frequency interval that includes the determined attraction point, wherein the frequency interval includes the first and the second dominant frequency values, and wherein the first dominant frequency value substantially relates to the second dominant frequency value over the frequency interval; and
        output the identified frequency interval to a visual display.

2. The system of claim 1, wherein to generate the first frequency distribution and the second frequency distribution, the processor is configured to utilize at least one Fourier transform, Short-Time Fourier transform, or a Wavelet transform.

3. The system of claim 1, wherein to generate the first frequency distribution and/or the second frequency distribution, the processor is configured to generate a spectrogram of the first signal and/or the second signal.

4. The system of claim 1, wherein the first or second dominant frequency value is substantially equal to a maximum frequency value, a chirp, a sustained maximum frequency value, a local maximum frequency value and/or a dominant frequency characteristic.

5. The system of claim 1, the processor being further configured to determine a dominant frequency threshold value, wherein the maximum frequency value and/or the local maximum frequency value is greater than or substantially equal to the dominant frequency threshold value.

6. The system of claim 1, wherein the first dominant frequency is substantially equal to the second dominant frequency, and wherein the first dominant time point is substantially equal to the second dominant time point.

7. The system of claim 1, the processor being further configured to identify a time interval, wherein the time interval includes the first and second time points, and wherein the first dominant frequency value substantially relates to the second dominant frequency value over the time interval.

8. The system of claim 1, the processor being further configured to collect a signal from a third electrode over a time period, wherein the processor generates a third dominant frequency value and wherein the attraction point is defined when the first, second and third dominant frequency values substantially relate to each other.

9. The system of claim 8, the processor being further configured to collect a signal from a third electrode over a time period, wherein the processor generates a third dominant frequency value and wherein the frequency interval includes the first, the second and the third dominant frequency values, and wherein the first, second and third dominant frequency values substantially relate to each other over the frequency interval.

10. The system of claim 1, wherein the first time-frequency distribution, the second time-frequency distribution, or both time-frequency distributions include a plurality of attraction points that define a plurality of modes of electrical activation patterns corresponding to an anatomical feature.

11. The system of claim 10, the processor being further configured to deconstruct the plurality of modes so that a tailored therapy can be directed to the electrical activation pattern and corresponding anatomical feature.

12. A system for mapping the electrical activity of the heart, the system comprising:
  a catheter shaft;
  a plurality of electrodes coupled to the catheter shaft; and
  a processor coupled to the catheter shaft, wherein the processor is configured to:
    receive a plurality of signals corresponding to signals sensed by the plurality of electrodes;
    generate a time-frequency distribution for each of the plurality of signals;
    identify a common dominant frequency of more than one of the plurality of electrodes, wherein the common dominant frequency occurs at a common dominant time point common to the one or more of the plurality of electrodes, and wherein to identify a common dominant frequency includes determining an attraction point, wherein the attraction point is defined when the common dominant frequency characteristic, the common dominant frequency and the common dominant time point are substantially equivalent; and
    create a visual display corresponding to the common dominant frequency.

13. The system of claim 12, wherein the dominant frequency characteristic includes a maximum frequency value, a chirp, a sustained maximum frequency value or a local maximum frequency.

14. The system of claim 12, wherein to create a visual display the processor is configured to create a phase map.

15. The system of claim 14, wherein the phase map displays one or more sinusoids corresponding to the plurality of signals or derivatives thereof.

16. A method for mapping the electrical activity of the heart, the method comprising:
  collecting a first signal corresponding to the first electrode and a second signal corresponding to the second electrode, wherein collecting the first and second signals occurs over a time period, and wherein the first and second signals are collected with a catheter having a plurality of electrodes;
  generating a first time-frequency distribution corresponding to the first signal;
  identifying a first dominant frequency value occurring at a first dominant frequency and a first time point;
  generating a second time-frequency distribution corresponding to the second signal;
  identifying a second dominant frequency value occurring at a second dominant frequency and a second time point;
  determining an attraction point, wherein the attraction point is defined when the first dominant frequency value substantially relates to the second dominant frequency value;
  identifying a time interval, wherein the time interval includes the first and second time points, and wherein the first dominant frequency value substantially relates to the second dominant frequency value over the time interval; and
  outputting the determined attraction point and the identified time interval to a visual display.

17. The method of claim 16, further comprising identifying a frequency interval, wherein the frequency interval includes the first and the second dominant frequency values, and wherein the first dominant frequency value substantially relates to the second dominant frequency value over the frequency interval.

18. The method of claim 16, further comprising: collecting a signal from a third electrode over a time period; and generating a third dominant frequency value, wherein the attraction point is defined when the first, second and third dominant frequency values substantially relate to each other.

19. The method of claim 18, further comprising identifying a frequency interval, wherein the frequency interval includes the first, the second and the third dominant frequency values, and wherein the first, second and third dominant frequency values substantially relate to each other over the frequency interval.

* * * * *